United States Patent
Davies

(10) Patent No.: US 7,868,291 B2
(45) Date of Patent: Jan. 11, 2011

(54) INVESTIGATION OF VEHICLE GLAZING PANELS

(75) Inventor: Christopher Davies, Kidwelly (GB)

(73) Assignee: Carglass Luxembourg Sarl-Zug Branch, Zug (CH)

( * ) Notice: Subject to any disclaimer, the term of this patent is extended or adjusted under 35 U.S.C. 154(b) by 0 days.

(21) Appl. No.: 11/571,173

(22) PCT Filed: Jun. 27, 2005

(86) PCT No.: PCT/GB2005/002510

§ 371 (c)(1),
(2), (4) Date: Jan. 7, 2008

(87) PCT Pub. No.: WO2006/000803

PCT Pub. Date: Jan. 5, 2006

(65) Prior Publication Data

US 2008/0094611 A1    Apr. 24, 2008

(30) Foreign Application Priority Data

Jun. 28, 2004    (GB) ................................ 0414394.7

(51) Int. Cl.
*G01J 3/00* (2006.01)
(52) U.S. Cl. .................... 250/330; 250/334; 250/338.1; 250/559.01; 250/559.4; 250/559.45; 356/239.8; 356/237.1; 356/239.1
(58) Field of Classification Search .................. 250/330, 250/334, 338.1, 559.01, 559.4, 559.45; 356/51, 356/239.7, 239.8, 237.1, 239.1, 239.2
See application file for complete search history.

(56) References Cited

U.S. PATENT DOCUMENTS

| 2,042,526 | A | | 6/1936 | Hohmann |
| 4,492,477 | A | * | 1/1985 | Leser .......................... 356/430 |
| 4,647,197 | A | | 3/1987 | Kitaya et al. |
| 4,665,392 | A | * | 5/1987 | Koontz ........................ 340/674 |
| 4,808,813 | A | * | 2/1989 | Champetier .................. 356/338 |
| 5,016,099 | A | | 5/1991 | Bongardt et al. |
| 5,245,403 | A | | 9/1993 | Kato et al. |
| 5,311,276 | A | | 5/1994 | Masao et al. |
| 5,452,079 | A | * | 9/1995 | Okugawa .................. 356/239.1 |
| 5,459,330 | A | | 10/1995 | Venaille et al. |
| 5,790,247 | A | * | 8/1998 | Henley et al. ............ 356/237.1 |
| 5,940,176 | A | | 8/1999 | Knapp |
| 6,011,620 | A | * | 1/2000 | Sites et al. ............... 356/239.1 |
| 6,052,534 | A | * | 4/2000 | Goto ........................... 396/71 |
| 6,088,116 | A | * | 7/2000 | Pfanstiehl .................... 356/445 |
| 6,115,118 | A | | 9/2000 | Dunnegan |
| 6,198,529 | B1 | | 3/2001 | Clark |
| 6,323,477 | B1 | | 11/2001 | Blasing et al. |

(Continued)

FOREIGN PATENT DOCUMENTS

DE    4318358    12/1994

(Continued)

*Primary Examiner*—David P Porta
*Assistant Examiner*—Djura Malevic
(74) *Attorney, Agent, or Firm*—Gordon & Jacobson, PC

(57) ABSTRACT

The condition of a glazing panel (2) is investigated using a viewing device (1) to view an illuminating electromagnetic radiation profile at a target zone. Data relating to the viewed radiation profile is compared to datum data, to produce an output related to the condition of the glazing panel at the target zone.

17 Claims, 1 Drawing Sheet

U.S. PATENT DOCUMENTS

| | | | |
|---|---|---|---|
| 6,570,651 B1 | 5/2003 | Haubold et al. | |
| 7,232,332 B2 * | 6/2007 | Osborn et al. | 439/487 |
| 7,283,227 B2 * | 10/2007 | Dureiko | 356/239.1 |
| 7,343,038 B2 * | 3/2008 | Tanaka et al. | 382/168 |
| 2004/0233421 A1 * | 11/2004 | Weinhold | 356/237.1 |
| 2007/0165213 A1 * | 7/2007 | Fang et al. | 356/239.1 |

FOREIGN PATENT DOCUMENTS

| | | |
|---|---|---|
| DE | 10102557 | 8/2002 |
| EP | 0497649 A1 | 8/1992 |
| EP | 1424551 A1 | 6/2004 |
| FR | 2396971 | 2/1979 |
| GB | 1526930 | 10/1978 |
| JP | 49089428 | 8/1974 |
| WO | WO 02/090952 A1 | 11/2002 |
| WO | WO 2006/000803 | 1/2006 |
| WO | WO 2006/029536 | 3/2006 |

* cited by examiner

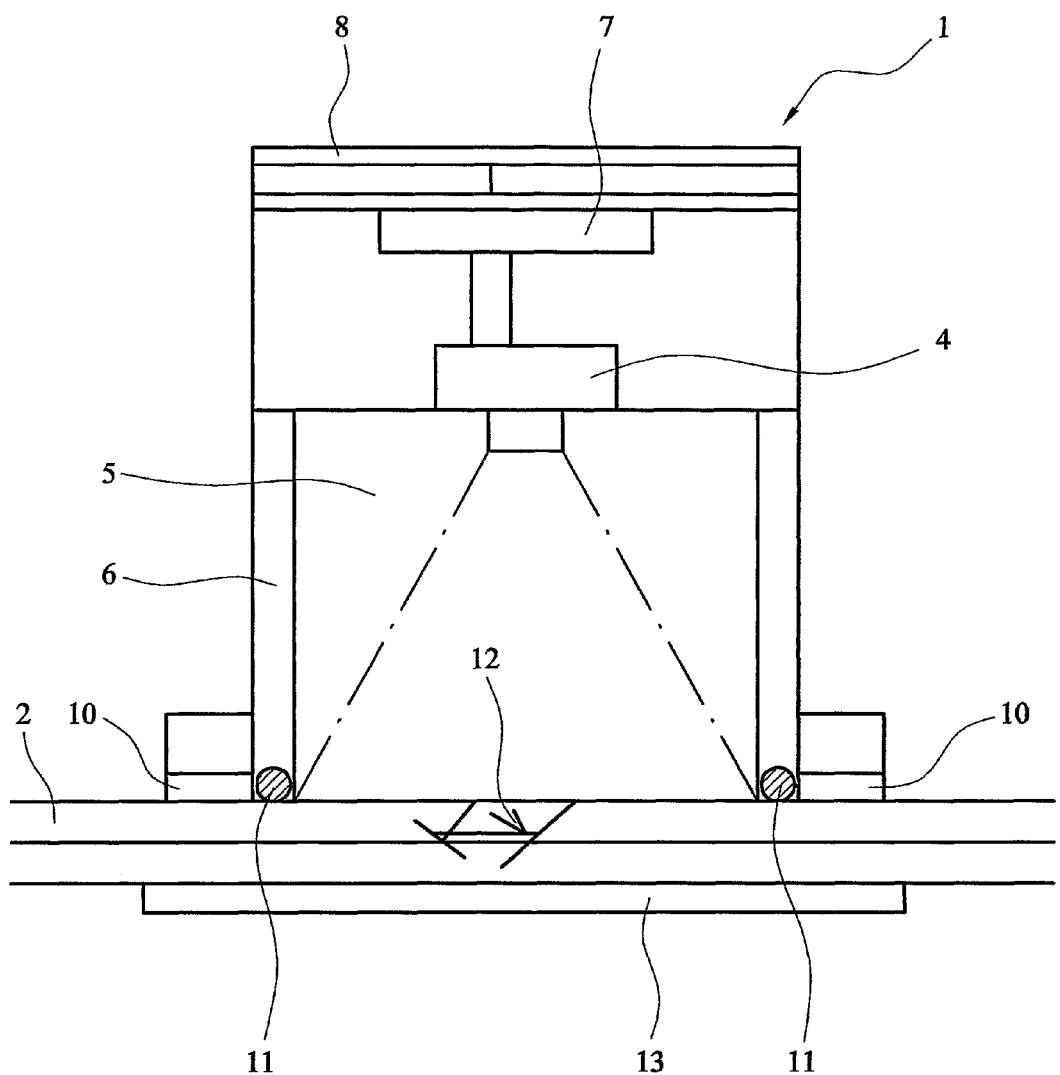

INVESTIGATION OF VEHICLE GLAZING PANELS

BACKGROUND OF THE INVENTION

1. Field of the Invention

The present invention relates to investigation of vehicle glazing panels particularly to assess the condition or structural integrity of the subject glazing panel. The invention has particular, although not exclusive, application in assessing the degree of damage to a windscreen having a flaw such as a break, crack or pit, and/or the quality of repair effected to such breaks, cracks, or pits.

2. State of the Art

Repairs are sometimes effected to vehicle glazing panels as an alternative to replacement, depending upon the severity, location and nature of the crack or break. Typically, during the repair procedure, resin is introduced into the flaw crack or break and the resin subsequently cures. The resin is selected such that, when cured, the optical characteristics of the resin repair match as closely as possible the optical characteristics of the material of the glazing panel. Often the resin is applied under partial vacuum or negative pressure to facilitate degassing of the resin and the crack or break in certain circumstances problems can occur in effecting a repair of adequate quality.

Certain prior art techniques have been proposed for investigating glazing panel condition using light transmission or scattering. Exemplary prior art techniques are disclosed in, for example, DE-A-19716809 and DE-A-3640891. An improved technique has now been devised.

SUMMARY OF THE INVENTION

The present invention seeks to provide a consistent and accurate means of investigating the condition of a glazing panel. The term glazing panel should be interpreted broadly to cover non glass panels in addition to glass panels (including laminated and non-laminated glazing panels).

According to a first aspect, the present invention provides an investigation method for investigating the condition of a glazing panel, the method comprising using a viewing device to view an illuminating electromagnetic radiation profile at a target zone of the glazing panel, wherein data relating to the viewed radiation profile is compared to other (datum) data, to produce an output related to the condition of the glazing panel at the target zone.

According to another aspect, the invention provides apparatus for investigating the condition of a glazing panel, the apparatus comprising:
- a viewing device to view an illuminating electromagnetic radiation profile at a target zone of the glazing panel;
- a processor to process data related to the viewed illuminating radiation profile viewed by the viewing device; and,
- an output device in communication with the processor and arranged to produce an output related to the condition of the glazing panel at the viewed target zone.

It is preferred that data relating to the viewed illuminating radiation profile is compared to system stored data. Preferably, the datum or stored data is either data relating to a non flawed zone of the glazing panel, or data bank data for a glazing panel of same type, or measured data from a flawed zone of the screen prior to repair. Beneficially, the stored data relates to a viewed illuminating radiation profile for a non flawed glazing panel viewed zone.

It is preferred that a readable output is given relating to the condition of the glazing panel.

It is preferred that an illuminating radiation delivery arrangement is arranged to direct radiation into the body of the glazing panel in order to enhance viewing of the radiation profile. Beneficially, the radiation delivery arrangement includes a radiation delivery ring extending at least partially about the target zone targeted by the viewing device.

The viewing device is preferably tuned to the wavelength, wavelength band, or region of the spectrum of the illuminating radiation. In one embodiment, radiation in the non-visible region of the spectrum is directed into the body of the glazing panel in order to facilitate viewing. The radiation selected may be infra red radiation directed into the body of the glazing panel in order to facilitate viewing. In certain circumstances, the use of infra red may be preferred due to the sensitivity of certain CCD cameras to such frequencies of radiation. In another embodiment light in the visible range of the spectrum may be utilised. Beneficially the light is of a restricted band width or individual wavelength. However, broadband, multiple wavelength sources (such as white light sources) may work adequately.

It is preferred that the viewing device comprises an image capture device. The viewing device beneficially comprises a multiplicity of radiation sensitive pixels. Desirably the viewing device is arranged to produce an electronic data output. In one embodiment the viewing device beneficially comprises an electronic camera device.

In one embodiment, the technique and apparatus utilise a dark space chamber spacing the viewing device from the target zone. Beneficially, the dark space chamber is provided with a distal end to be placed in register with the glazing panel, the distal end preferably including a light seal to contact the glazing panel. Advantageously, the radiation delivery arrangement is peripherally positioned relative to the dark space chamber.

In one embodiment the viewing device, processor and output device are provided integrally in a hand held unit.

In an alternative embodiment, the processor may be situated remotely from the viewing device and output device.

In one realisation of the technique in accordance with the invention, the flaw zone is viewed by the apparatus before and after repair and an output generated to quantify or gauge the quality of the repair.

In an alternative or complementary realisation of the technique of the invention, the flaw zone is viewed after repair and an output generated to quantify or gauge the quality of repair.

It is preferred that a backing is positioned opposed to the viewing apparatus adjacent a reverse face of the glazing panel, in order to enhance the viewing process.

In a general realisation of the invention light or other selected radiation is transmitted through the body of the glazing panel providing background illumination as viewed by the viewing device. Light/radiation interaction with a flaw (crack or break) present in the glazing panel at the target zone causes contrast or discontinuity in the illumination profile viewed, when compared with the background illumination. The viewing device provides an output signal to the processor enabling the viewed situation to be compared to a datum situation or ideal. The output device enables a quality value or gauge output (such as pass or fail) to be produced.

The invention will now be described in a specific embodiment and by way of example only, with reference to the accompanying drawing.

BRIEF DESCRIPTION OF THE DRAWING

The FIGURE is a schematic representation of an apparatus according to the invention for use in performance of the method according to the invention.

DETAILED DESCRIPTION OF THE PREFERRED EMBODIMENTS

Referring to the drawing there is shown apparatus in accordance with the invention comprising a hand held manually manipulatable and positionable device 1 for investigating the condition of a windscreen 2. The device 1 comprises a housing 3 containing a CCD camera 4 positioned at a proximal end of a dark space chamber 5, defined by a peripheral chamber wall 6. The distal end of chamber 5 is either open (as shown in the drawing) or may include a window transmissible to illuminating radiation. A filter may be provided to inhibit certain wavelength radiation from passing into the chamber. The CCD camera 4 targets a viewing field at the distal end of the chamber 5.

Peripherally of the chamber housing wall 6 and at the distal end of the chamber is mounted an annular array of LED's 10 arranged to output illuminating radiation in the red light wavelength region of the visible spectrum. The LED's direct illuminating light into the body of the glass and provide a background 'glow' of illuminating radiation at the target view field of the camera 4. LED light sources are preferred due to commercial availability of LED light sources of high quality and low power. The camera views the radiation profile at the glazing panel zone at the target view field. This may be the uniform radiation 'glow' at undamaged/unrepaired portions within the view field, or a contrast/discontinuity profile caused by a crack or break, or repaired crack or break. The illuminating radiation input to the camera pixel array gives spatial and total illumination data for the target view field. The distal end of the chamber 5 is provided with a compressible seal 11, to enable the device to be held against the glazing panel without causing damage, and to prevent ambient radiation leaking into the chamber 5. A dark backing strip 13 may be applied to the rear of the glazing panel to provide contrast and enhance the 'glow' effect in the body of the glazing panel.

The output from the camera 4 passes to a processor 7 which is able to store and compare data output from the camera, as will be described in greater detail hereafter. The processor outputs to an output display 8 which gives a readable indication of the condition of the glazing panel to an operative using the device.

In use, the device can be held against a known undamaged portion of a glazing panel and operated to record datum situation data. As an alternative datum data for a particular glazing panel may be stored, for example in a database. The device may then be operated with a break or crack 12 in the camera view field to record data for the damaged area of the glazing panel. The crack or break 12 is then repaired (typically by filling the break or crack with resin which is subsequently cured) and the repaired break or crack is then subjected to test. The repaired break or crack data can be compared with either or both of the previously recorded data (for the undamaged screen and the unrepaired crack or break). The data can be processed to give a quality level output (for example as a percentage of ideal result or percentage improvement over the damaged situation) or a gauge output, such as repair 'pass' or 'fail'.

It should be readily understood that the processor could be situated remotely from the device and communication in real time provided between the local apparatus and the processor enabling the system to operate. Furthermore the data could be downloadable for post processing remotely.

The invention claimed is:

1. A system for investigating a glazing panel, the system comprising:
   a hand-holdable housing having a distal end and a wall defining an internal dark space chamber;
   an electronic infra-red image capture device supported within said housing and facing said dark space chamber;
   a compressible light seal provided at said distal end of said housing to enable the housing to be held against the glazing panel in a region of a target zone to be investigated;
   an annular array of infra-red light emitters positioned at said distal end of said housing peripherally about said dark space chamber, wherein said wall is disposed between said annular array of infra-red light emitters and said infra-red image capture device;
   a processor to process data related to captured image data from the electronic infra-red image capture device; and
   an output device in communication with the processor and adapted to produce an output related to a condition of the glazing panel at the target zone.

2. A system according to claim 1, wherein:
   the system is configured to compare data relating to a captured image to system stored data.

3. A system according to claim 2, wherein:
   the stored data relates to a captured image for a non-flawed glazing panel viewed zone.

4. A system according to claim 1, wherein:
   the image capture device comprises a multiplicity of radiation sensitive pixels.

5. A system according to claim 1, wherein:
   the image capture device comprises an electronic camera device.

6. A system according to claim 1, wherein:
   the annular array of infra-red light emitters are configured to direct infra-red light into the glazing panel in order to facilitate viewing of a radiation profile by the infra-red image capture device.

7. A system according to claim 1, wherein:
   the system is configured to view a flaw zone before and after a repair and to generate an output to quantify or gauge a quality of the repair.

8. A system according to claim 1, wherein:
   the system is configured to view a flaw zone after a repair and to generate an output to quantify or gauge a quality of the repair.

9. A system according to claim 1, further comprising:
   a backing positioned opposite the housing adjacent a reverse face of the glazing panel in order to enhance a viewing process.

10. A system according to claim 1, wherein:
    the image capture device, the processor, and the output device are provided integrally in the housing.

11. A system according to claim 1, wherein:
    the processor is situated remotely from the hand held device.

12. A method of investigating a glazing panel, comprising:
    providing a system according to claim 1;
    using the system to capture an image of a glazing panel; and
    using the output device of the system to produce an output related to a condition of the glazing panel for investigation thereof.

13. A system according to claim 1, wherein:

said compressible light seal is adapted to contact the glazing panel when the housing is held against the glazing panel.

14. A system according to claim 1, wherein:

said annular array of light emitters are disposed adjacent a distal end of said wall.

15. A system according to claim 1, wherein:

said annular array of light emitters are disposed adjacent said compressible seal.

16. A system according to claim 1, wherein:

said wall includes an interior surface opposite an exterior surface, and wherein said annular array of light emitters are disposed adjacent and exterior to said exterior surface of said wall.

17. A system according to claim 1, wherein:

said dark space chamber has a proximal end, and said infra-red image capture device is positioned at said proximal end of the dark space chamber.

* * * * *